(12) United States Patent
Dennis et al.

(10) Patent No.: US 6,258,065 B1
(45) Date of Patent: *Jul. 10, 2001

(54) SURGICAL INSTRUMENT SEAL ASSEMBLY

(75) Inventors: William G. Dennis; Michael E. Prosek, both of Jacksonville, FL (US)

(73) Assignee: Core Dynamics, Inc., Jacksonville, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/434,608

(22) Filed: Nov. 5, 1999

Related U.S. Application Data

(60) Provisional application No. 60/126,356, filed on Mar. 26, 1999.

(51) Int. Cl.⁷ ............................. A61M 5/178; A61M 5/14
(52) U.S. Cl. ............................. 604/167.03; 604/167.01; 604/167.06; 604/256
(58) Field of Search .................... 604/164, 167, 604/171, 256, 537; 251/149.1; 285/302

(56) References Cited

U.S. PATENT DOCUMENTS

| | | |
|---|---|---|
| 4,929,235 | 5/1990 | Merry et al. . |
| 4,960,412 | 10/1990 | Fink . |
| 5,053,013 | 10/1991 | Ensminger et al. . |
| 5,147,336 * | 9/1992 | Wendell et al. ............ 604/283 |
| 5,180,373 | 1/1993 | Green et al. . |
| 5,269,763 | 12/1993 | Boehmer et al. . |
| 5,304,143 | 4/1994 | Green et al. . |
| 5,308,336 | 5/1994 | Hart et al. . |
| 5,385,553 | 1/1995 | Hart et al. . |
| 5,391,153 | 2/1995 | Haber et al. . |
| 5,456,284 | 10/1995 | Ryan et al. . |
| 5,476,475 | 12/1995 | Gadberry . |
| 5,492,304 | 2/1996 | Smith et al. . |
| 5,496,280 | 3/1996 | Vanderbroek et al. . |
| 5,562,632 | 10/1996 | Davila et al. . |
| 5,603,702 | 2/1997 | Smith et al. . |
| 5,628,732 * | 5/1997 | Antoon, Jr. et al. ............ 604/167 |
| 5,643,227 | 7/1997 | Stevens . |
| 5,709,664 | 1/1998 | Vandenbroek et al. . |
| 5,720,730 | 2/1998 | Blake, III . |
| 5,727,770 | 3/1998 | Dennis . |
| 5,741,228 | 4/1998 | Lambrecht et al. . |
| 5,752,938 | 5/1998 | Flatland et al. . |
| 5,820,600 | 10/1998 | Carlson et al. . |
| 5,820,604 | 10/1998 | Fox et al. . |
| 5,848,997 | 12/1998 | Erskine et al. . |

* cited by examiner

Primary Examiner—Richard K. Seidel
Assistant Examiner—Michael Hayes
(74) Attorney, Agent, or Firm—McGuireWoods, LLP

(57) ABSTRACT

A surgical instrument valve assembly is provided with a valve seal where the upper portion of the valve seal is rigidly mounted to the body of the valve assembly. The lower portion of the valve seal is configured to allow some radial movement while the upper portion of the valve seal remains rigidly mounted within the valve assembly. The valve seal may be provided with stay that prevents the valve seal from inverting when an instrument in withdrawn from the valve assembly.

35 Claims, 7 Drawing Sheets

SURGICAL INSTRUMENT SEAL ASSEMBLY

This application claims the benefit of Provisional Application No. 60/126,356 filed on Mar. 26, 1999, which is incorporated herein by reference in its entirety.

FIELD OF THE INVENTION

The present invention relates broadly to medical devices used during surgical procedures and, more particularly to a surgical instrument seal assembly for selective mounting to a cannula for the insertion of a surgical instrument therethrough while maintaining a fluid seal around the instrument.

BACKGROUND OF THE INVENTION

In certain types of surgery, a cannula is used to provide a passageway into a body cavity through which surgical instruments may be passed. Cannulas are typically elongate rod-like members having a bore therethrough the surgical instrument may be passed through the bore. At times, the body cavity will be insufflated by a gas and at all times, the cannula will be subjected to internal body fluids. Therefore, some form of seal assembly is necessary to allow the surgical instrument to pass while maintaining sealed integrity around the instrument such that the insufflation gas, the internal body fluids, or both, cannot escape.

Typically, in conventional devices, such a seal mechanism will include a housing for mounting on the cannula, with the housing having a bore therethrough for passage of the surgical instrument. Two seals are typically located within the housing. The lower housing contains a seal, typically called a duckbill valve that assists maintaining gases and fluids in place when an instrument is not inserted within the duckbill valve. The duckbill valve is typically formed from flexible material and includes a slit opening that gives way to the instrument upon insertion. The upper housing typically includes a valve seal that includes a relative wide access opening and a relatively narrow valve opening. The valve opening can expand to accommodate the surgical instrument and is sufficiently resilient to form a seal around the instrument upon insertion.

SUMMARY OF THE INVENTION

However, certain problems have been identified in conjunction with use and operation of conventional devices. Initially, the elastomeric material of the valve seal can be damaged by contact with the surgical instrument upon insertion. As a result, seal protectors have been used. The seal protectors are units separate from the valve seal and disposed intermediate the seal and a surgical instrument. Some seal protectors include complex lever arrangements that may engage and open the valve opening while acting as a barrier between the instrument and the valve seal. Other approaches include the application of rigid plastic leaf-like members in an overlapping, circular array in abutment with the valve seal. The overlapping arrangement allows the leaves to open upon insertion of an instrument. These approaches have been generally costly and complex.

Another problem with conventional devices has been the inability of the valve opening to align with the instrument if the instrument is inserted "off axis," i.e., out of alignment with the throughbore in the valve seal. Attempts to resolve this problem have resulted in special mounting arrangements for the valve seal wherein the valve seal is laterally displaceable within a housing holding the valve seal. These solutions have required additional material and can be expensive and complex.

Therefore, there is a need for a surgical instrument sealing assembly that provides protection for the valve seal during contact with the instrument, especially during off axis insertion of the instrument, that is inexpensive and simple to produce.

It is accordingly an object of the present invention to provide a surgical instrument seal assembly having a valve seal that can withstand impact from a surgical instrument.

As another object of the present invention a seal assembly is provided that protects the valve seal upon off axis insertion of a surgical instrument.

It is another object of the present invention to provide a seal assembly that is simple and easy to produce.

Accordingly, a surgical instrument seal assembly is provided as described in the description of the exemplary embodiments. The present invention provides a unitary valve seal that includes an armor reinforcement that is unitarily formed with the elastomeric seal material and protects the integrity of the elastomeric seal material during insertion of the surgical instrument. Further, the valve seal is configured to allow some off-axis movement of a valve opening in the valve seal while a mounting portion of the valve seal itself remains rigidly mounted within its housing. Thus, while the upper portion of the valve seal may be incapable of lateral movement, the valve opening itself can shift a small amount to accommodate an off-axis instrument insertion.

The surgical instrument seal assembly for mounting to a cannula for the insertion of a surgical instrument therethrough while maintaining a fluid seal around the instrument is provided with an upper body portion having an upper surface that defines a throughbore extending completely through the seal assembly. A lower body portion projects below the upper body portion and the lower body portion defines a cannula receiving opening adapted to mount the valve seal assembly on the cannula. The valve assembly is provided with a unitary valve seal that has an upper seal portion having a mounting portion rigidly mounted in the upper body portion adjacent the interior portion of the upper surface wherein the upper seal portion is mounted about the throughbore and a lower seal portion extending from the upper seal portion adapted to seal around the instrument.

Further, in accordance with an aspect of the invention, the surgical instrument seal assembly is provided with a stay wherein at least a portion of the stay is incapsulated in the valve seal. The stay may be unitarily formed with the lower seal portion.

The surgical instrument seal assembly, in accordance with an aspect of the invention, is further provided with an upper seal portion and a lower seal portion integrally formed from the same material and wherein the valve seal further comprises a stay partially incapsulated in the lower seal portion.

Still further, in accordance with an aspect of the invention, the surgical instrument seal assembly is provided with a valve seal formed from an elastomeric material.

The surgical instrument seal assembly, in accordance with an aspect of the invention. may be provided with a duckbill valve in the lower body portion.

In one embodiment, the surgical instrument seal assembly is provided with a stay that is adapted to resist inversion of the valve seal when an instrument is withdrawn from the valve seal.

The surgical instrument seal assembly, in accordance with an aspect of the invention, may be provided with a stay made from a material selected from the group consisting of polyethylene, polypropylene, nylon, and plastic elastomers. The stay of the surgical instrument valve assembly may be shaped to substantially match the lower seal portion.

In accordance with an aspect of the invention, the surgical instrument seal assembly is provided with a stay wherein at least a portion of the stay is incapsulated in at least a portion of the lower seal portion.

Still further, in accordance with an aspect of the invention, the surgical instrument seal assembly may be provided with a stay having a circumferential flange above at least a portion of the stay incapsulated in the lower seal portion.

The surgical instrument seal assembly, in accordance with an aspect of the invention, is provided with a stay wherein at least a portion of the stay is approximately frustoconocal in shape.

The surgical instrument seal assembly, in accordance with an aspect of the invention, may be provided with a stay where the stay has a plurality of flexible members.

Still further, in accordance with the aspect of the invention, the surgical instrument seal assembly may be provided with a stay wherein the stay has a lower portion incapsulated by the valve seal material and forms a unitary structure.

In accordance with an aspect of the present invention, a valve seal for use in a surgical instrument scale assembly is provided with an upper seal portion, a lower seal portion extending from the upper seal portion, and a stay wherein at least a portion of the stay is incapsulated in the lower portion of the valve seal.

In accordance with an aspect of the present invention, the valve seal may be provided with a stay that is unitarily formed with the lower seal portion. Further, the upper seal portion and the lower seal portion may be integrally formed from the same material. Further, the valve seal may be formed from elastomeric material. The elastomeric material may be selected from the group consisting of silicone, plastic elastomers, polyisoprene, butyl rubber, neoprene, and natural rubber.

Still further in accordance with an aspect of the present invention, the stay may be adapted to resist inversion of the valve seal when an instrument is withdrawn from the valve seal. Further, the stay may be made from materials select from the group consisting of polyethylene, polypropylene, nylon, and plastic elastomers. Still further, the stay may be shaped to substantially match the shape of the lower seal portion.

In accordance with another aspect of the present invention, the stay may further comprise circumferential flange above the at least a portion of the stay incapsulated in the lower seal portion. Further, the stay may include a circumferential upper wall disposed above the circumferential flange. Still further, at least a portion of the stay may be approximately frustoconical in shape. The stay may be provided with a plurality of flexible members. In accordance with another aspect of the present invention, the stay may have a lower portion that is incapsulated by the valve seal material and forms a unitary structure.

BRIEF DESCRIPTION OF THE DRAWINGS

These and other aspects of the invention will become apparent from the following descriptions which illustrate exemplary embodiments of the invention when read in conjunction with the accompanying drawings, in which.

DESCRIPTION OF THE PREFERRED EMBODIMENTS

Figure 1:
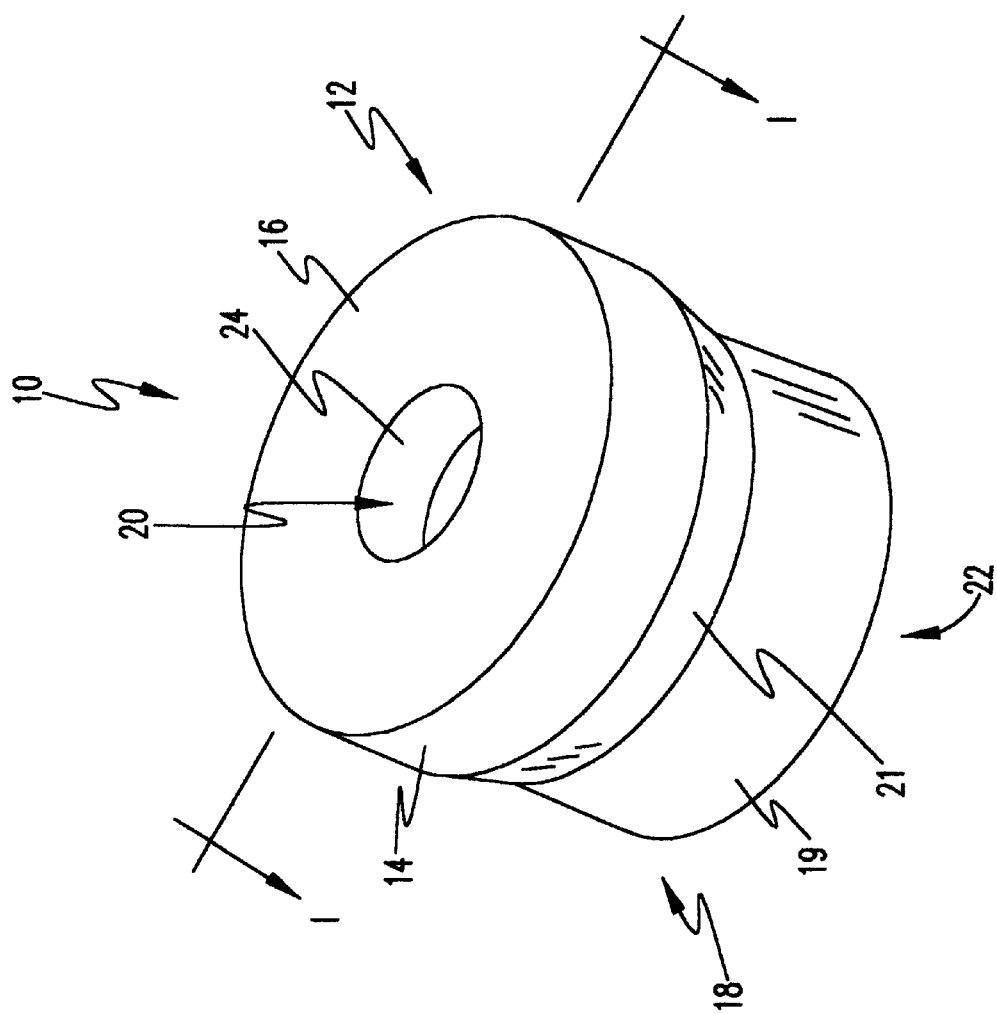
FIG. 1 is a perspective view of a surgical instrument with a seal assembly according to an exemplary embodiment of the present invention.

With reference to the drawings, wherein like numerals have been used to represent like features, and, more particularly to FIG. 1, a surgical instrument valve seal assembly 10 is illustrated and includes an upper body portion 12 and a lower body portion 18. The upper body portion 12 is generally cylindrical and includes a washer-shaped upper surface 16 integrally formed with a generally cylindrical sidewall 14. A throughbore 20 is provided at the center of the upper surface 16 with the throughbore 20 extending completely through the seal assembly 10. A generally cylindrical protector wall member 24 is integrally formed with upper surface 16 at the throughbore 20 to project inwardly into the interior of the upper body portion 12 to both strengthen the structure and to guide the surgical instrument into the throughbore 20.

The lower body portion 18 includes a generally cylindrical wall 19 projecting below the upper body portion 12. A tapered transition wall 21 is disposed intermediate the cylindrical lower wall 19 and the upper body portion 12, and acts to taper the diameter of the seal assembly 10 from the larger upper body portion 12 to the smaller lower body portion 18. A cannula receiving opening 22 is formed in the lower body portion 18 for mounting the device on a cannula (not shown). It should be recognized that the upper body portion 12, the transition wall 21, and the lower body portion 18 may be formed from molded polymeric material for ease of manufacture.

Figure 2:
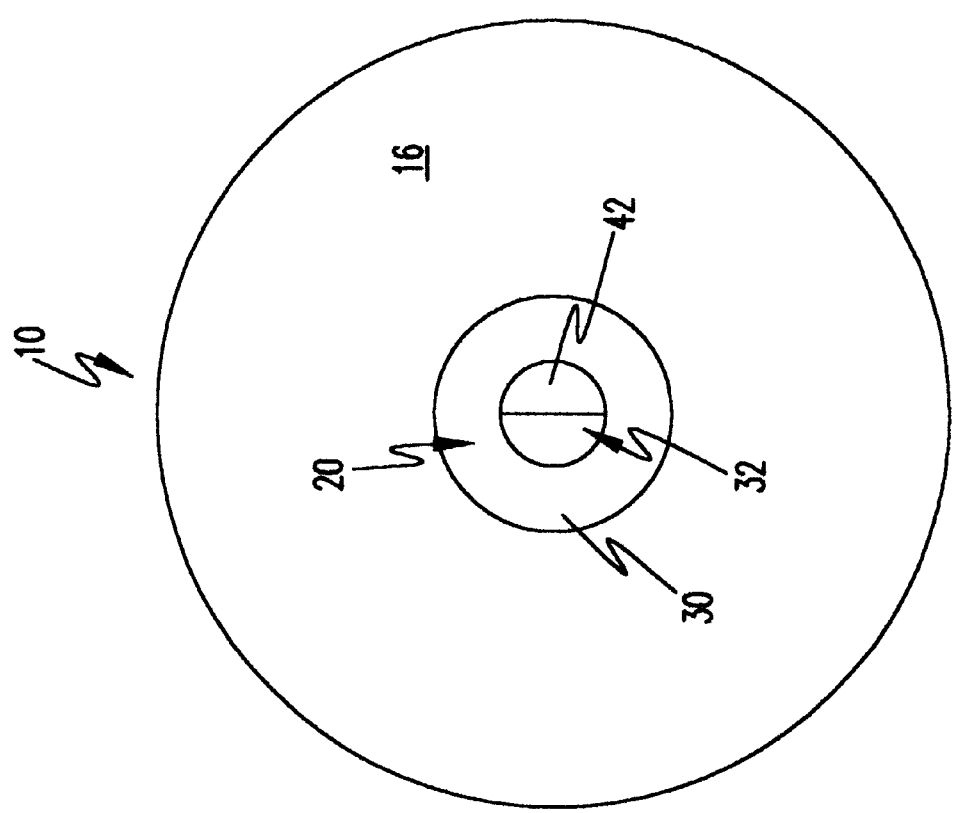
FIG. 2 is a top plan view of the seal assembly illustrated in FIG. 1 in accordance with an exemplary embodiment of the present invention.

With reference to FIG. 2, it can be seen that the throughbore 20 provides access to the valve seal 30 and a duckbill valve 42, both of which will be explained in greater detail hereinafter.

Figure 3:
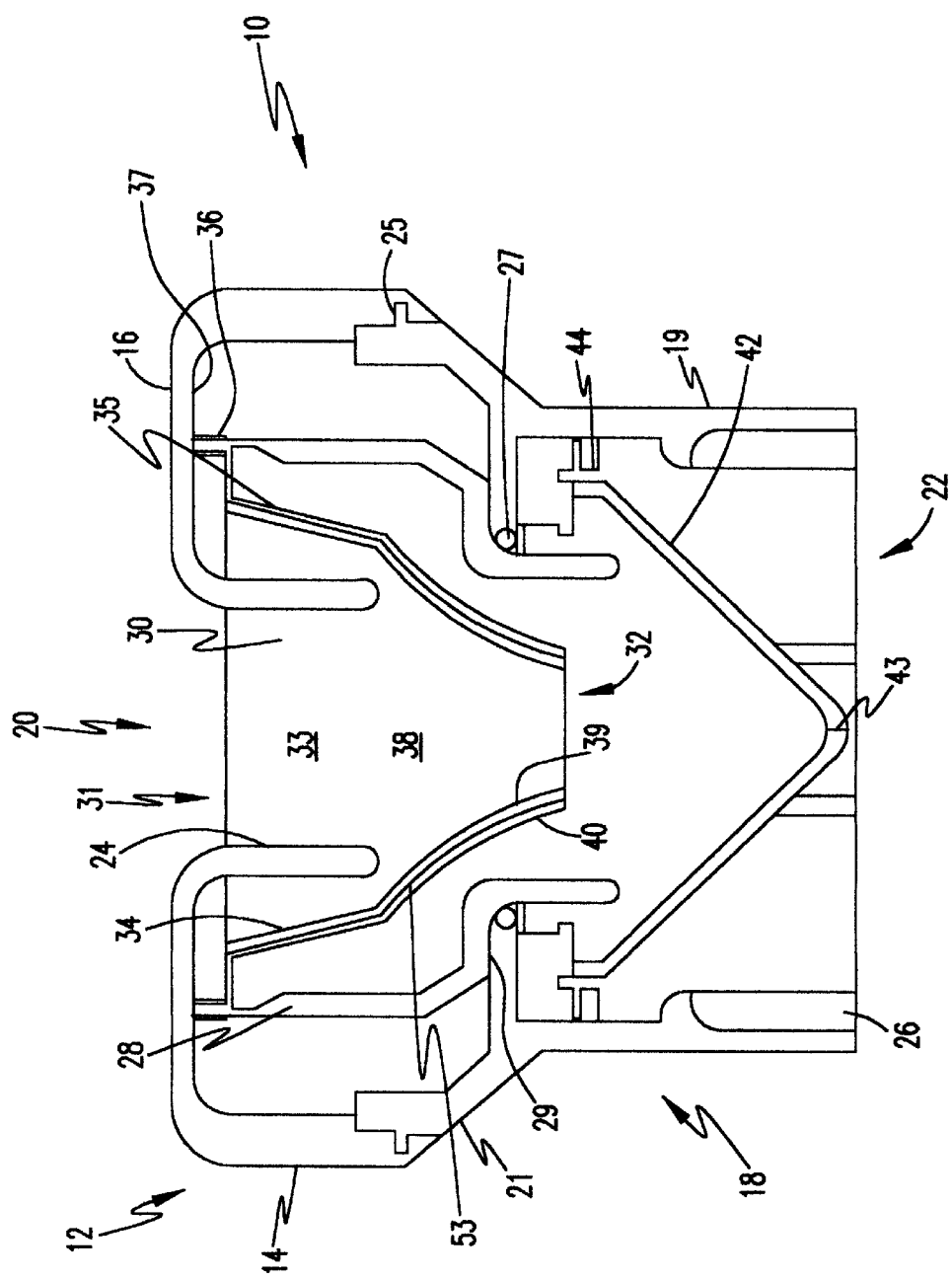
FIG. 3 is a cross-sectional view of the seal assembly illustrated in FIG. 1 taken along lines I—I in accordance with an exemplary embodiment of the present invention.

Turning now to FIG. 3, a cross-sectional view of the seal assembly 10 illustrated in FIG. 1 reveals the structure of the seal assembly 10, in accordance with an exemplary embodiment of the present invention. It can be seen that the upper body portion 12 is mounted to the lower body portion 18 with a shoulder 25 formed on the transition wall 21. The shoulder 25 engages a similar shoulder formed on the cylindrical wall 14 of the upper body portion 12. The two piece construction provides for ease of assembly during manufacture.

Inner support member 28 projects downwardly from an interior portion 37 of the upper body portion 12, opposite to the upper surface 16, into engagement with a shoulder 29 formed on the lower body portion 18. The inner support member 28 provides stability for the seal assembly and a mounting location for a valve seal 30. Preferably, an o-ring 27 is located between the inner support member 28 and shoulder 29 to form a substantially leak-tight seal between the upper body portion 12 and the lower body portion 18.

Figure 4:
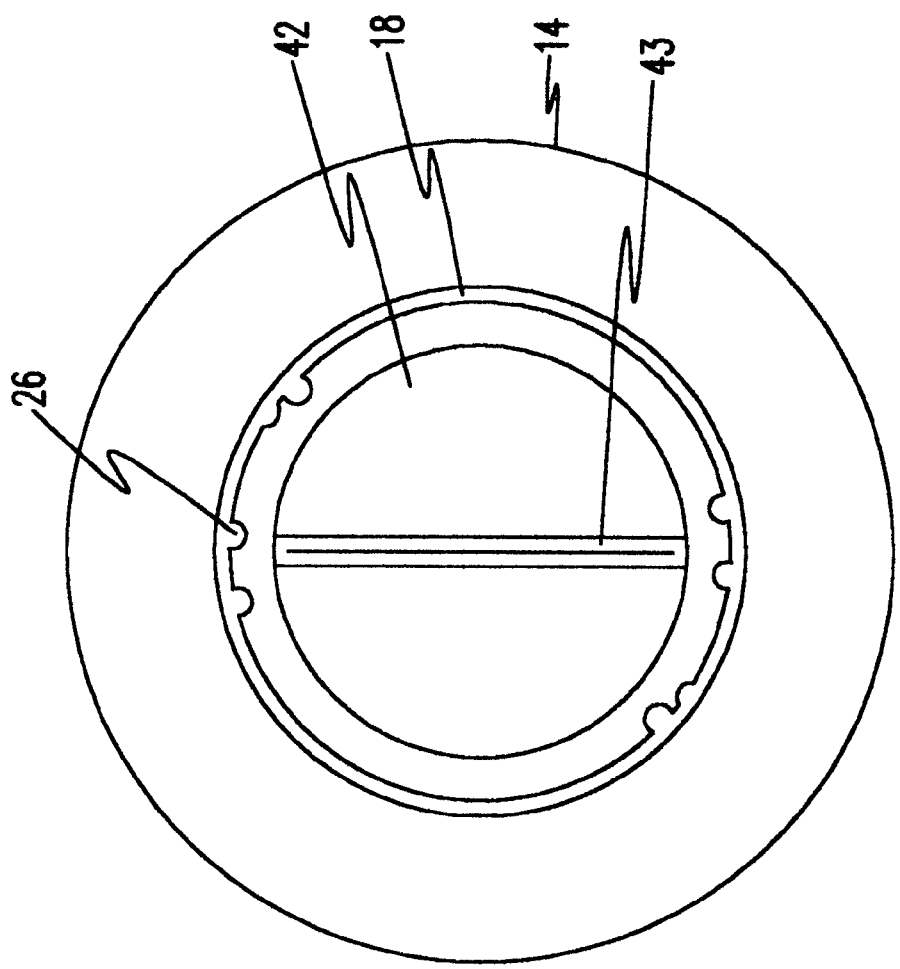
FIG. 4 is a bottom view of the seal assembly shown in FIG. 3 in accordance with an exemplary embodiment of the present invention.

As shown in FIG. 4 with continuing reference to FIG. 3, the lower body portion 18 is configured for mating engagement with a cannula and, accordingly, includes mating members 26 formed adjacent the cannula opening 22 in the lower body portion 18. For example, the mating members 26 may be a plurality of ribs.

A duckbill valve 42 is formed as an elastomeric member disposed in the lower body portion 18 using a mounting assembly 44. The duckbill valve 42 includes a slit-like opening 43 that forms a seal, and allows for an instrument to be inserted through the cannula. Further, the duckbill valve 42 acts as an initial barrier to gases and fluids.

Turning now the valve seal 30, a mounting portion 41 of valve seal 30 is rigidly mounted in the upper body portion 12 at a mounting member 36 on the inner support member 28. That is, the valve seal 30 is mounted adjacent the interior portion 37 opposite to the upper surface 16. The valve seal 30, including the mounting member 36 and the inner support member 28, is rigidly mounted within the upper body portion 12 and incapable of lateral shifting, within the upper body portion 12, with respect to either the mounting member 36 or the inner support member 28.

The valve seal 30 is formed as a generally frusto-conical member having two distinct portions defined by respective differently tapered walls. Specifically, the valve seal 30 is formed as an elastomeric member having a reinforcing layer 53 formed therewith. This structure provides the flexibility necessary to expand the valve opening 32 yet protects the valve seal 30 from damage from a surgical instrument. An upper seal portion 33 includes an upper inner wall 34 and an upper outer seal wall 35, both formed as a generally unitary portion having a first taper. A lower seal portion 38 is integrally formed with the upper seal portion 33 and includes a lower inner seal wall 39 formed unitarily with a lower outer seal wall 40. The lower seal portion 38 includes a taper that is more sloped and curved than the upper seal portion 33. The reinforcing layer 53 may be the inner seal wall 39 or the outer seal wall 40. Alternatively, the reinforcing layer 53 may be sandwiched between the inner seal wall 39 and the outer seal wall 40.

Accordingly, the upper seal portion 33 of the valve seal 30 tapers from a relatively wide access opening 31 to the lower seal portion 38 where the taper is increased to extend the lower seal portion 38 to the instrument seal opening 32. Further, in one embodiment the lower seal portion 38 may be curved slightly inwardly rather than being a straight conical taper. This construction allows the seal opening 32 to move radially, at least a small distance to accommodate an off axis instrument insertion. Further, the reinforcing layer 53 of the unitary valve seal body provides protection against punctures by an instrument and resists inversion of the valve seal 30 when an instrument is withdrawn from the valve seal. It should be noted that the valve seal 30 may be formed as a single layer without having the reinforcing layer 53 formed within. Such a single layer would be formed from a material that provides advantages similar to the unitary valve seal body described above with respect to puncture resistance, flexibility and sealing capability.

Figure 5:
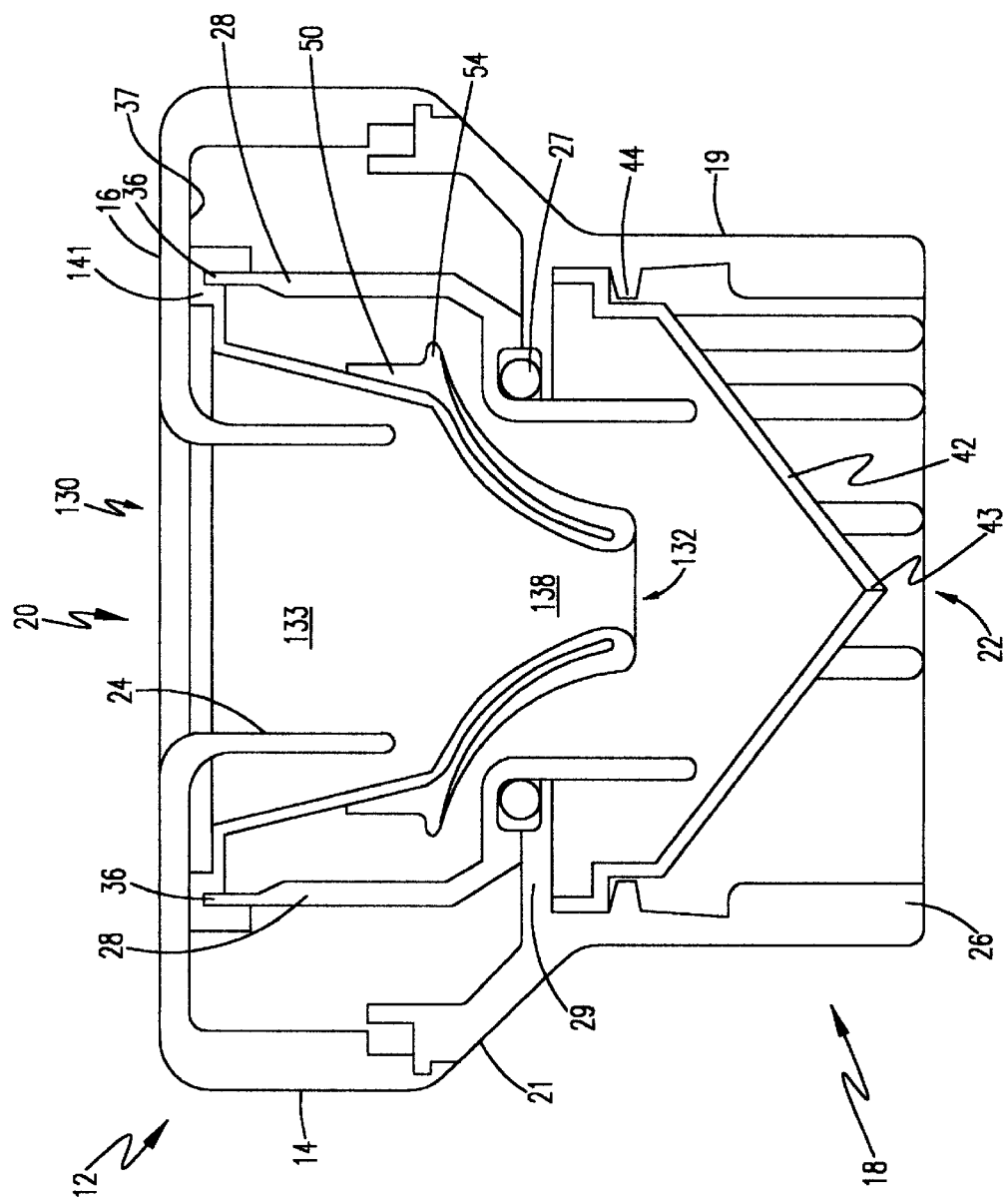
FIG. 5 is a cross-sectional view of another embodiment of the seal assembly illustrated in FIG. 1 taken along lines I—I in accordance with an exemplary embodiment of the present invention.

With reference now to FIG. 5, an alternate exemplary embodiment of the valve seal shown generally as 130 is shown therein. The mounting portion 141 of valve seal 130 is rigidly mounted in the upper body portion 12 at a mounting member 36 on the inner support member 28 adjacent the interior portion 37, which opposes the upper surface 16. The mounting portion 141 of valve seal 130, including the mounting member 36 and the inner support member 28, is rigidly mounted within the upper body portion 12 and incapable of shifting laterally with respect to the upper body portion 12. The valve seal 130 is substantially similar in shape to the valve seal 30 described above except that the lower seal portion 138 is formed with a reinforcing stay 50 described in detail below.

Figure 6:
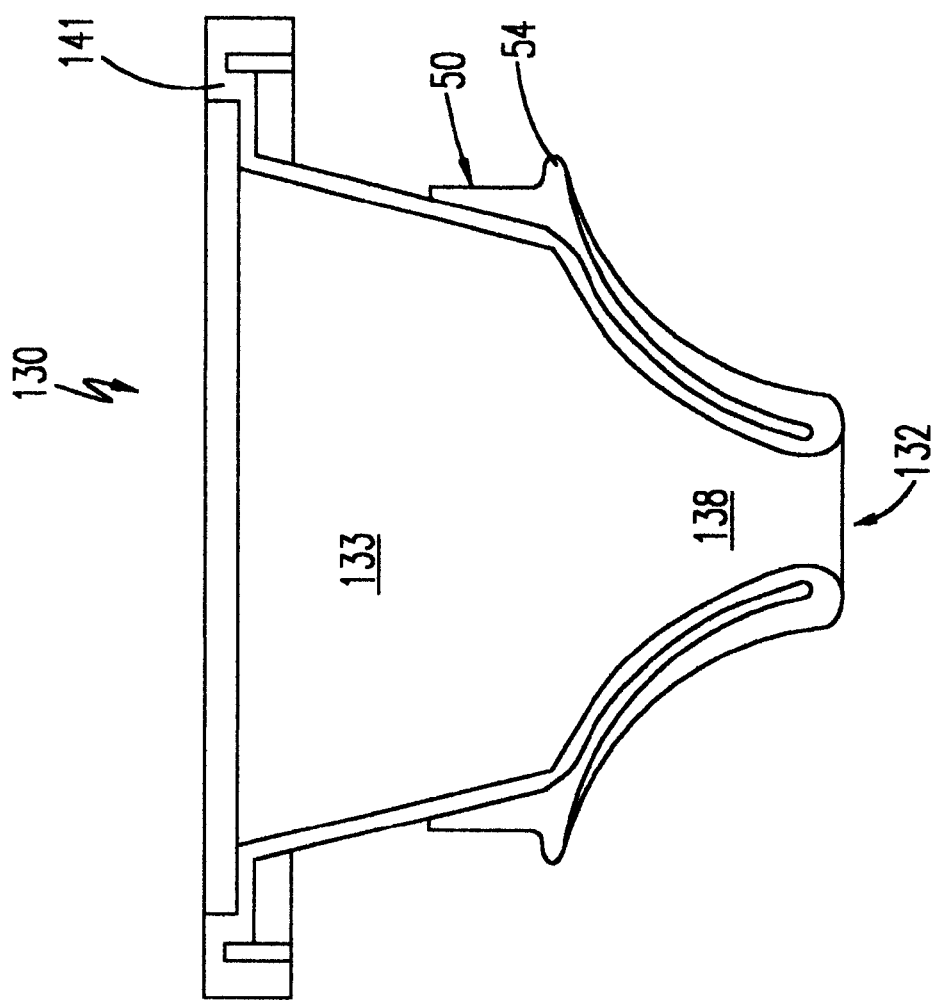
FIG. 6 is a cross-sectional view of the valve seal shown in FIG. 5 in accordance with an exemplary embodiment of the present invention.

With reference now to FIG. 6, the position of the reinforcing stay 50 in the valve seal 130 is shown. In an exemplary embodiment, the stay 50 is shaped and sized to approximately match the shape of lower seal portion 138 of the valve seal 130 and at least a portion of the upper seal portion 133 of the valve seal 130. At least a portion of the reinforcing stay 50 is incapsulated in the lower seal portion 138 of the valve seal 130 to form a unitary structure.

Figure 8:
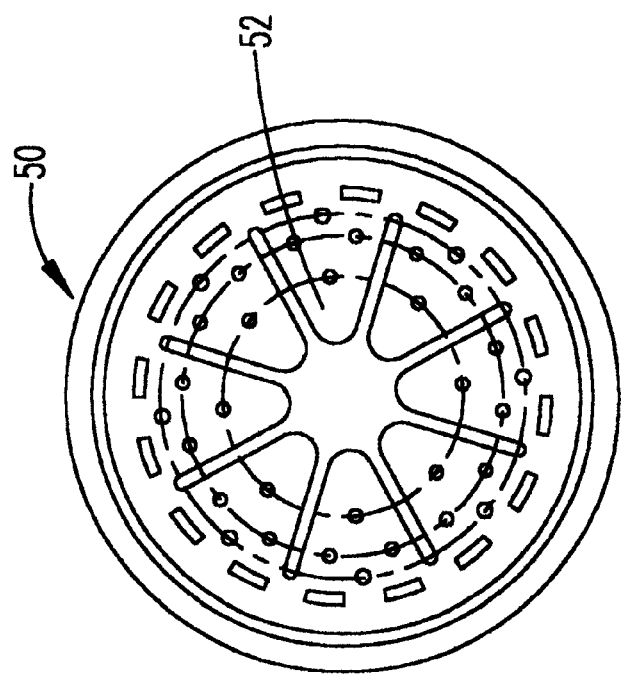
FIG. 8 is a top plan view of the stay shown in FIG. 7 in accordance with an exemplary embodiment of the present invention.
Figure 7:
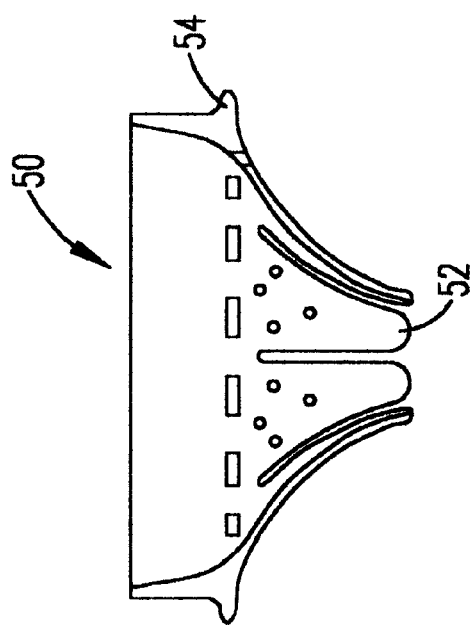
FIG. 7 is a side view of the stay used in the valve seal in accordance with an exemplary embodiment of the present invention.

As shown in FIGS. 7 and 8, the portion of the reinforcing stay 50 that is shaped to match the lower portion 138 of the valve seal 130 preferably contains a plurality of flexible reinforcing members 52. The plurality of flexible members 52 allows the stay 50 to flex proportionally with the elastomeric material of the valve seal when an instrument is inserted through the valve opening 132. The stay 50 also substantially resists inversion of the valve seal 130 when an instrument is withdrawn from the valve seal 130. Additionally, in an exemplary embodiment, the stay 50 has a circumferential flange 54 around the outside of the stay located above the flexible members 52. As best shown in FIG. 5, the circumferential flange 54 prevents the upper seal portion 133 from being pushed into the lower half of inner support member 28. That is, the circumferential flange 54 will come into contact with the lower half of the inner support member 28 upon bending of the upper seal portion 133. Additionally, the stay 50 includes a circumferential upper wall 56 as shown in FIGS. 6 and 7. The upper wall 56 is disposed above the circumferential flange 54 and adjacent to the upper seal portion 133.

The valve seals 30 and 130 are preferably made from elastomeric materials that are able to expand to accommodate a surgical instrument and form a seal around the instrument. In an exemplary embodiment the elastomeric material is able to resist puncturing from the instrument. Representative elastomeric materials include, but are not limited to, silicone. plastic elastomers, polyisoprene, butyl rubber, neoprene or natural rubber and the like.

Representative reinforcing layer materials are those materials sufficient to expand to accommodate a surgical instrument, resist puncturing from the instrument, form a seal around the instrument and capable of forming a unitary structure with the elastomeric material.

The stay 50, as shown in FIG. 5, for example, is made from a material that is able to resist inversion when an instrument is withdrawn from the valve seal. Further, the stay may be made from a material that is able to bond with the material of the valve seal 130 thereby forming a unitary structure. The bonding may occur by an adhesive or by any other suitable process, by chemical means known to one skilled in the art, or by any other suitable process. Suitable materials for the stay may include, but are not limited to polyethylene, polypropylene, nylons, plastic elastomers and the like.

In operation, the seal assembly 10 of the present invention is mounted to a cannula (not shown) using the mating members 26. A surgical instrument (not shown) is inserted into the throughbore 20 for passage through the instrument seal opening 32 and the duckbill valve 42. If the instrument is inserted off axis, the valve seal 30 resists puncture and the lower seal portion 38 allows some movement of the instrument seal opening 32 to accommodate the insertion of the instrument. Further, the curved taper of the lower seal portion 38 helps to guide the instrument toward the instrument seal opening 32. In an exemplary embodiment, the lower seal portion 38 has a curved taper from the bottom of the upper seal portion 33 to the seal opening of 32.

When the instrument passes through the instrument seal opening 32 the elastomeric nature of the valve seal 30 allows the opening( 32, to expand to accommodate the instrument. Typical openings may be 5 mm across in a relaxed state and may expand up to 12 mm to accommodate the instrument. It will be appreciated that the seal assembly may be constructed to accommodate various sizes of instruments. The lower seal walls 39 and 40 allow the instrument seal opening to fit snugly around the instrument to provide a fluid and gas seal. The instrument is then inserted through the duckbill valve 42. The instrument may then be inserted downwardly into the canntila and, eventually, into the body cavity.

When the valve seal 130 is used, the operation is similar to that described above. A surgical instrument (not shown) is inserted into the throughbore 20 for passage through the instrument seal opening 132 and the duckbill valve 42. If the instrument is inserted off axis, the protector wall 24 helps align the instrument and the valve seal 130 resists puncture. The lower body portion 138 allows some movement of the instrument seal opening 132 to accommodate the insertion of the instrument. Further, the curved taper of the lower seal portion 138 helps to guide the instrument toward the instrument seal opening 132. In an exemplary embodiment, the lower seal portion 138 has a curved taper from the bottom of the upper seal portion 133 to the seal opening of 132.

When the instrument passes through the instrument seal opening 132, the elastomeric nature of the valve seal 130 and the flexible members 52 of the stay 50 allows the opening 132 to expand to accommodate the instrument. As the instrument is inserted through the valve seal 130, the circumferential flange 54 on the stay 50 engages the inner support member 28 to help prevent the valve seal 130 from dislodging from the mounting member 36 and acts to prevent the upper seal portion 133 from being pushed into the lower half of inner support member 28. Typical openings may be 5 mm across in a relaxed state and may expand up to 12 mm to accommodate the instrument. It will be appreciated that the scale assembly may be constructed to accommodate various sizes of instruments. The lower seal portion 138 allows the instrument seal opening 132 to fit snugly around the instrument to provide a fluid and gas seal. The instrument is then inserted through the slit 43 in the duckbill valve 42. The instrument may then be inserted downwardly into the cannula and, eventually, into the body cavity. When the instrument is withdrawn from the valve seal assembly, the flexible members 52 of the stay 50 act to resist inversion of the valve seal.

By the above description, the present invention provides a simple, effective surgical instrument seal assembly. The surgical instrument seal assembly in accordance with the invention protects the valve seal from damage from off axis instrument insertions, is cost effective to produce and is durable.

It will therefore be readily understood by those persons skilled in the art that the present invention is susceptible to broad utility and application. Many embodiments and adaptations of the present invention other than those herein described, as well as many variations, modifications and equivalent arrangement, will be apparent from or reasonably suggested by the present invention and the foregoing description thereof, without departing from the substance or scope of the present invention.

Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations variations, modifications and equivalent arrangements the present invention being limited only by the claims and the equivalents thereof.

What is claimed is:

1. A surgical instrument seal assembly for mounting to a cannula for the insertion of a surgical instrument, the seal assembly comprising:

an upper body portion having an upper surface that defines a throughbore extending completely through the seal assembly;

a lower body portion projecting below the upper body portion wherein the lower body portion defines a cannula receiving opening adapted to mount the seal assembly on the cannula; and a unitary valve seal comprising:

an upper seal portion having a mounting portion and a generally frustoconical upper sealing member having a first taper extending from the mounting portion, wherein the mounting portion is rigidly mounted in the upper body portion adjacent an interior portion of the upper body portion, said interior portion opposing the upper surface, the upper seal portion being mounted about the throughbore; and a lower seal portion extending from the upper seal portion, the lower seal portion being adapted to seal around the surgical instrument and having a generally frusto-conical lower sealing member having a second taper that is different from the first taper, the lower sealing member including a lower seal wall having an inner wall portion and an outer wall portion, a reinforcing layer being disposed intermediate the inner wall portion and the outer wall portion.

2. The surgical instrument seal assembly of claim 1, wherein the valve seal further comprises a stay wherein at least a portion of the stay is incapsulated in the valve seal.

3. The surgical instrument seal assembly of claim 2, wherein the stay is unitarily formed with the lower seal portion.

4. The surgical instrument seal assembly of claim 2, wherein the stay is adapted to resist inversion of the valve seal when an instrument is withdrawn from the valve seal.

5. The surgical instrument seal assembly of claim 4, wherein the stay is made from a material selected from the group consisting of polyethylene, polypropylene, nylon, and plastic elastomers.

6. The surgical instrument seal assembly of claim 4 wherein the stay has a lower portion incapsulated by the valve seal material and forms a unitary structure.

7. The surgical instrument seal assembly of claim 2, wherein the stay is shaped to substantially match the lower seal portion.

8. The surgical instrument seal assembly of claim 2, wherein at least a portion of the stay is encapsulated in at least a portion of the lower seal portion.

9. The surgical instrument seal assembly of claim 8, wherein the stay further comprises a circumferential flange above the at least a portion of the stay encapsulated in at least a portion of the lower seal portion.

10. The surgical instrument seal assembly of claim 9, wherein the stay further includes a circumferential upper wall disposed above the circumferential flange.

11. The surgical instrument seal assembly of claim 2, wherein at least a portion of the stay is approximately frusto-conical in shape.

12. The surgical instrument seal assembly of claim 2, wherein the stay further comprises a plurality of flexible members.

13. The surgical instrument valve seal assembly of claim 1, wherein the upper seal portion and the lower seal portion are integrally formed from the same material and wherein the valve seal further comprises a stay that is partially incapsulated in the lower seal portion.

14. The surgical instrument seal assembly of claim 1, wherein the valve seal is formed from an elastomeric material.

15. The surgical instrument seal assembly of claim 14, wherein the elastomeric material is selected from the group consisting of silicone, plastic elastomers, polyisoprene, butyl rubber, neoprene and natural rubber.

16. The surgical instrument seal assembly of claim 1, further comprising a duckbill valve in the lower body portion.

17. The surgical instrument seal assembly of claim 1 wherein the reinforcing layer is integral with at least a portion of the inner wall portion.

18. The surgical instrument seal assembly of claim 1 wherein the generally frusto-conical lower sealing member has a lower seal wall extending from the upper sealing member and terminating in an instrument seal opening, the lower seal wall being curved inward and defining a concave outer surface of the lower sealing member.

19. The surgical instrument seal assembly of claim 1 wherein the throughbore is symmetrically formed around a bore axis, the upper sealing member defines an access opening adjacent the mounting portion and having a diameter larger than the throughbore, and the lower sealing member defines an instrument seal opening, and wherein the valve seal is configured so that upon insertion of an instrument in an orientation not aligned with the bore axis, the instrument seal opening will move radially relative to the bore axis and an instrument axis opening will remain substantially unmoved relative to the bore axis.

20. A valve seal assembly for use in a surgical instrument seal assembly, the valve seal comprising:

an upper seal portion having a generally frusto-conical upper sealing member having a first taper;
a lower seal portion extending from the upper seal portion wherein the lower seal portion is adapted to seal around the surgical instrument and has a generally frusto-conical lower sealing member having a second taper that is different from the first taper, the lower sealing member including a lower seal wall having an inner wall portion and an outer wall portion, a reinforcing layer being disposed intermediate the inner wall portion and the outer wall portion; and
a stay wherein at least a portion of the stay is incapsulated in the lower portion of the valve seal.

21. The valve seal of claim 20, wherein the stay is unitarily formed with the lower seal portion.

22. The valve seal of claim 20, wherein the upper seal portion and the lower seal portion are integrally formed from the same material.

23. The valve seal of claim 20, wherein the valve seal is formed from an elastomeric material.

24. The value seal of claim 23, wherein the elastomeric material is selected from the group consisting of silicone, plastic elastomers, polyisoprene, butyl rubber, neoprene and natural rubber.

25. The valve seal of claim 20, wherein the stay is adapted to resist inversion of the valve seal when an instrument is withdrawn from the valve seal.

26. The valve seal of claim 20, wherein the stay is made from a material selected from the group consisting of polyethylene, polypropylene, nylon, and plastic elastomers.

27. The valve seal of claim 20, wherein the stay is shaped to substantially match the lower seal portion.

28. The valve seal of claim 20, wherein the stay further comprises a circumferential flange above the at least a portion of the stay encapsulated in the lower seal portion.

29. The valve seal of claim 28, wherein the stay further includes a circumferential upper wall disposed above the circumferential flange.

30. The valve seal of claim 29, wherein the stay further comprises a plurality of flexible members.

31. The valve seal of claim 20, wherein the stay further comprises a plurality of flexible members.

32. The valve seal of claim 20, wherein at least a portion of the stay is approximately frusto-conical in shape.

33. The valve seal of claim 20, wherein the stay has a lower portion encapsulated by the valve seal material and forms a unitary structure.

34. The surgical instrument seal assembly of claim 20 wherein the generally frusto-conical lower sealing member has a lower seal wall extending from the upper sealing member and terminating in an instrument seal opening, the lower seal wall being curved inward and defining, a concave outer surface of the lower sealing member.

35. The surgical instrument seal assembly of claim 20 wherein the throughbore is symmetrically formed around a bore axis, the upper sealing member defines an access opening adjacent the mounting portion and having a diameter larger than the throughbore, and the lower sealing member defines an instrument seal opening, and wherein the valve seal is configured so that upon insertion of an instrument in an orientation not aligned with the bore axis, the instrument seal opening will move radially relative to the bore axis and an instrument axis opening will remain substantially unmoved relative to the bore axis.

* * * * *